United States Patent [19]

Debreczeni

[11] Patent Number: 5,462,534
[45] Date of Patent: Oct. 31, 1995

[54] NEEDLE ASSEMBLY FOR USE WITH A SYRINGE

[75] Inventor: Joe Debreczeni, Brossard, Canada

[73] Assignee: Moldex Plastics & Tool Inc., Canada

[21] Appl. No.: 340,633

[22] Filed: Nov. 16, 1994

[30] Foreign Application Priority Data

Oct. 19, 1994 [CA] Canada ............................ 2118458

[51] Int. Cl.⁶ .................................................. A61M 5/32
[52] U.S. Cl. ........................................ 604/192; 604/263
[58] Field of Search .................................. 604/192, 187, 604/198, 263, 110

[56] References Cited

U.S. PATENT DOCUMENTS

| | | | |
|---|---|---|---|
| 5,116,325 | 5/1992 | Paterson | 604/192 |
| 5,151,089 | 9/1992 | Kirk, III et al. | 604/263 X |
| 5,152,751 | 10/1992 | Kozlowski | 604/192 |
| 5,207,653 | 5/1993 | Janjua et al. | 604/192 |
| 5,232,455 | 8/1993 | Hollister | 604/263 X |

*Primary Examiner*—John D. Yasko
*Attorney, Agent, or Firm*—Miller & Christenbury

[57] ABSTRACT

The disclosure herein describes a needle assembly for use with a syringe which includes a needle device having a holder and a needle, and a needle guard which is defined by a hollow cylindrical sheath that partially surrounds the needle; the guard has a first end mounted to the needle holder and an opposite closed end in proximity to the needle pointed end. Elongated slots and pivot pins cooperate to anchor the needle guard to the holder. In one embodiment, the slots are provided on the needle guard and the pins on the holder while, in a second embodiment, the slots are provided on the holder and the pins on the guard. This cooperating arrangement of the slot and pins allows the sheath to be pivoted back at substantially 180° relative to its needle surrounding initial position thus removing the presence of the sheath as much as possible from the needle puncturing operation.

9 Claims, 4 Drawing Sheets

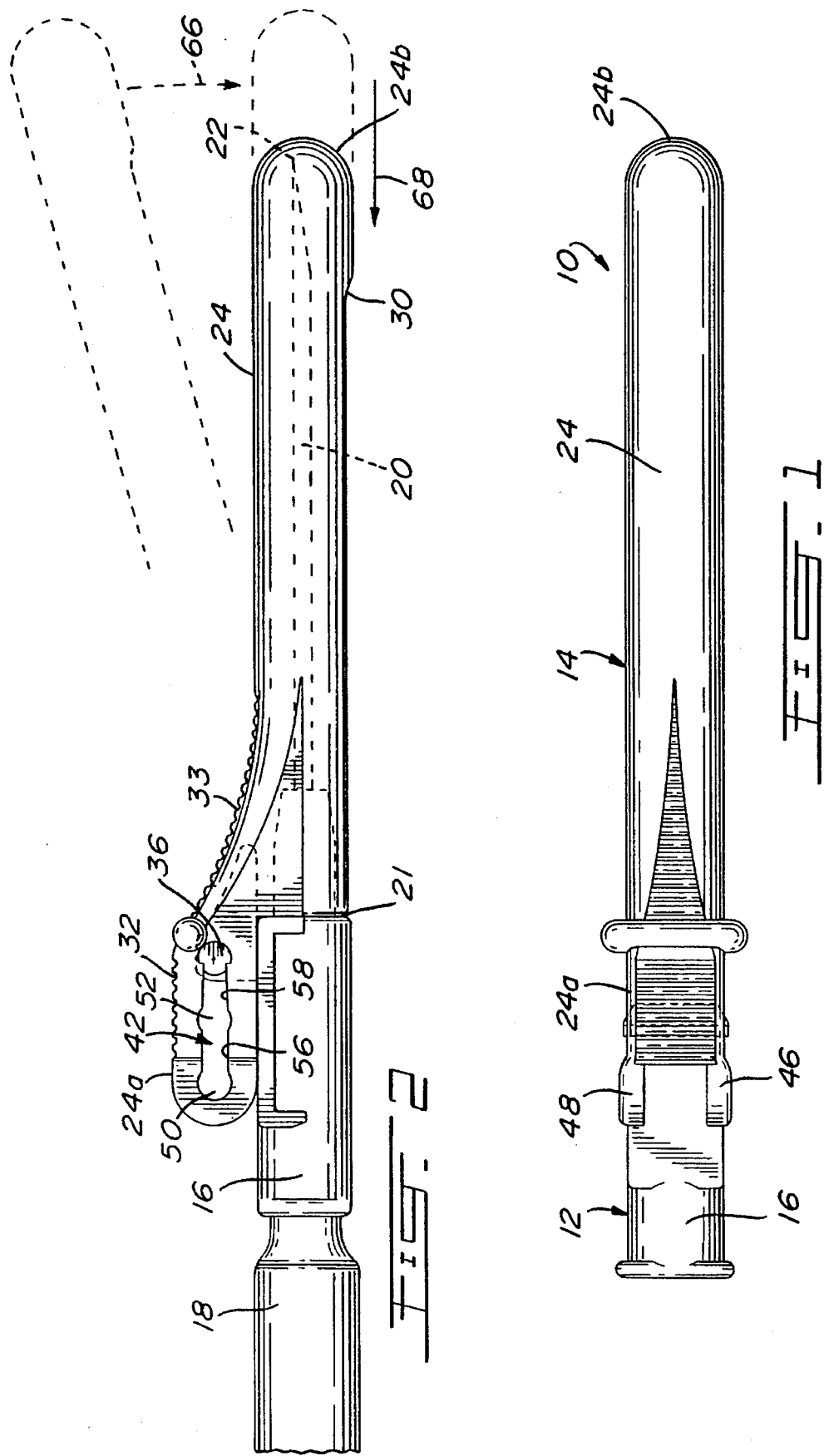

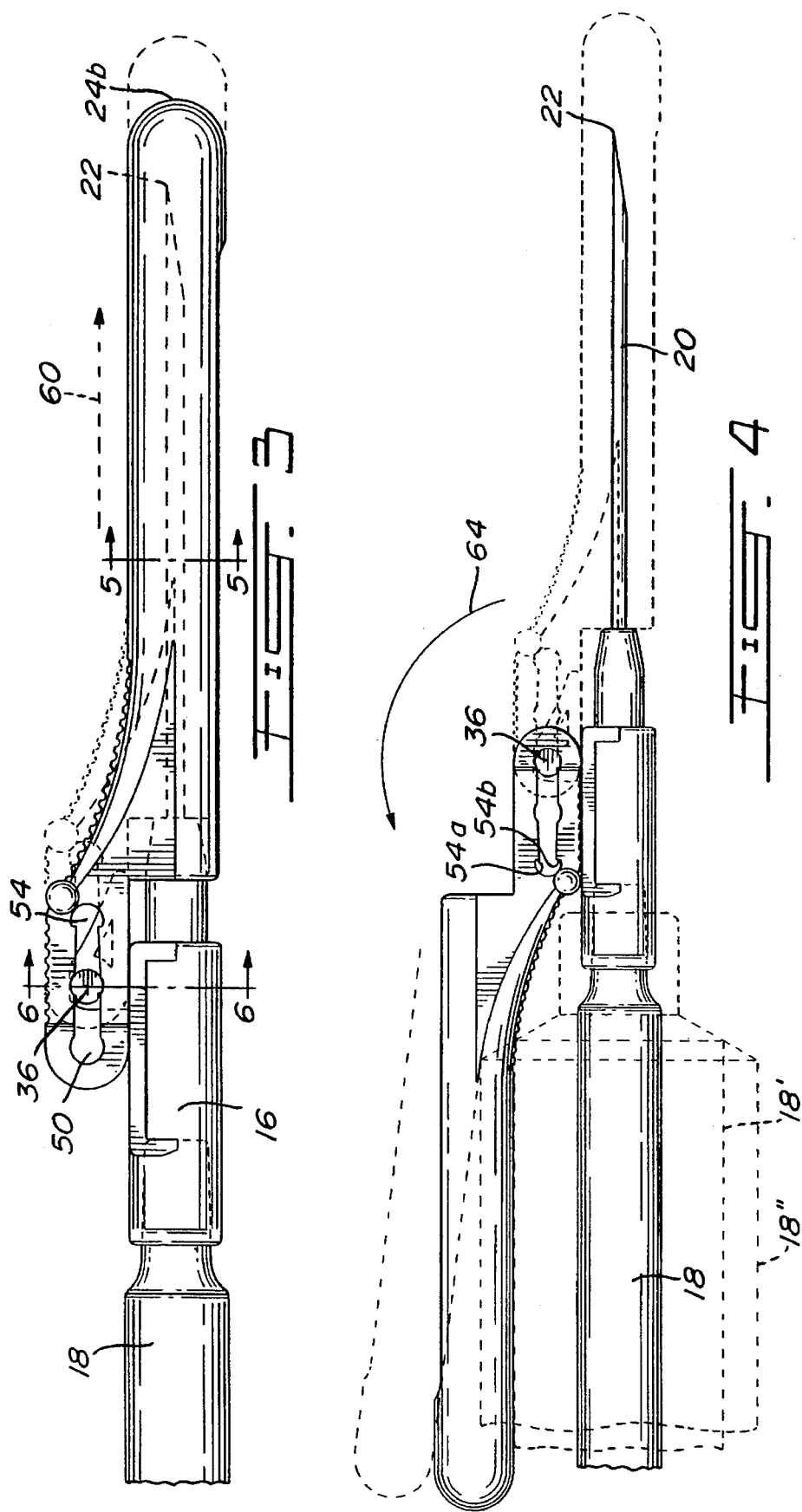

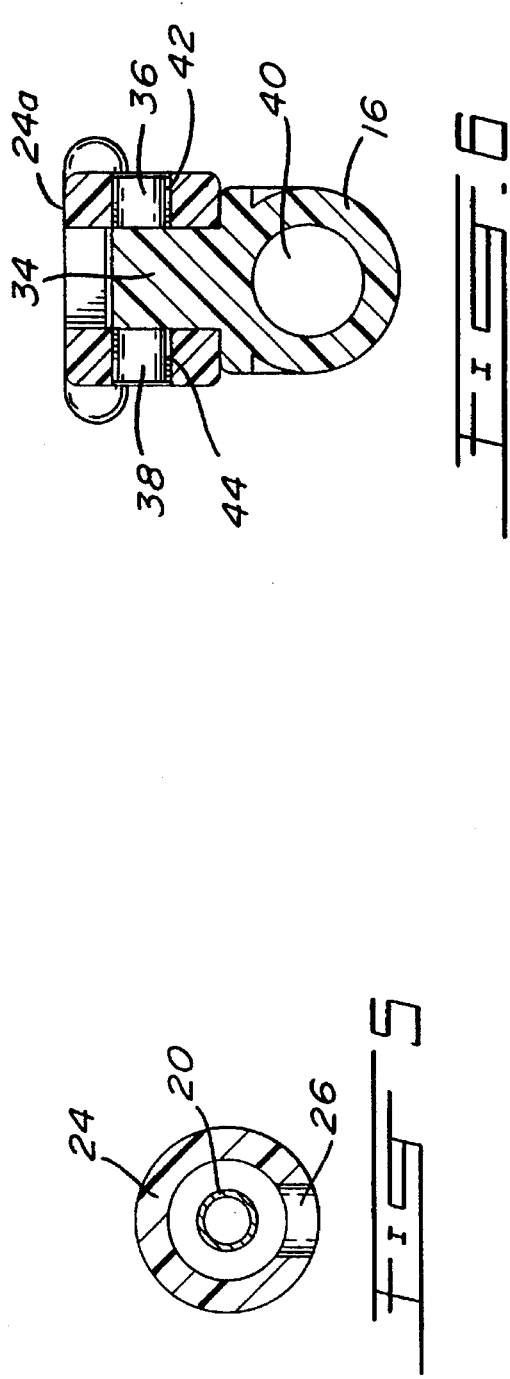
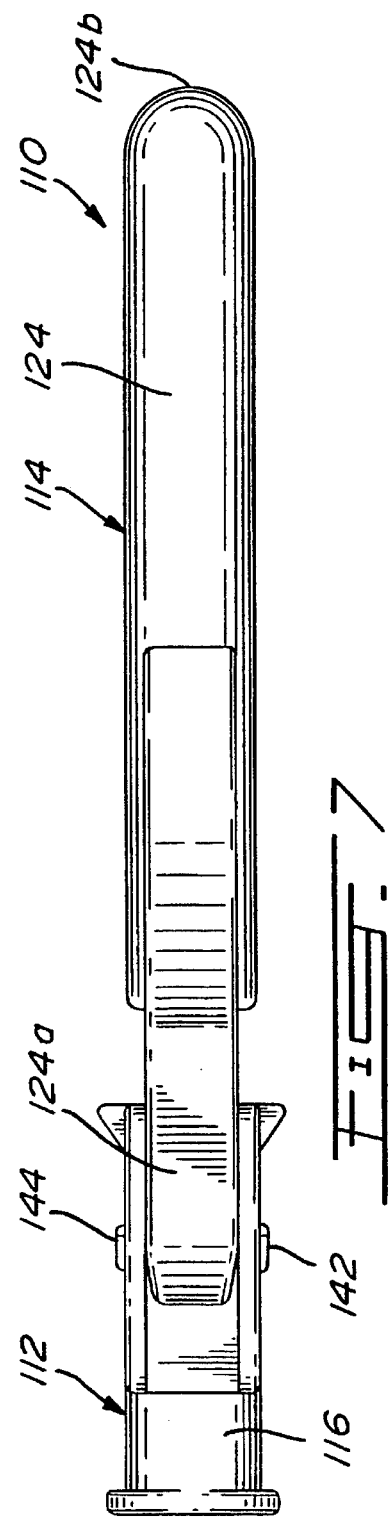

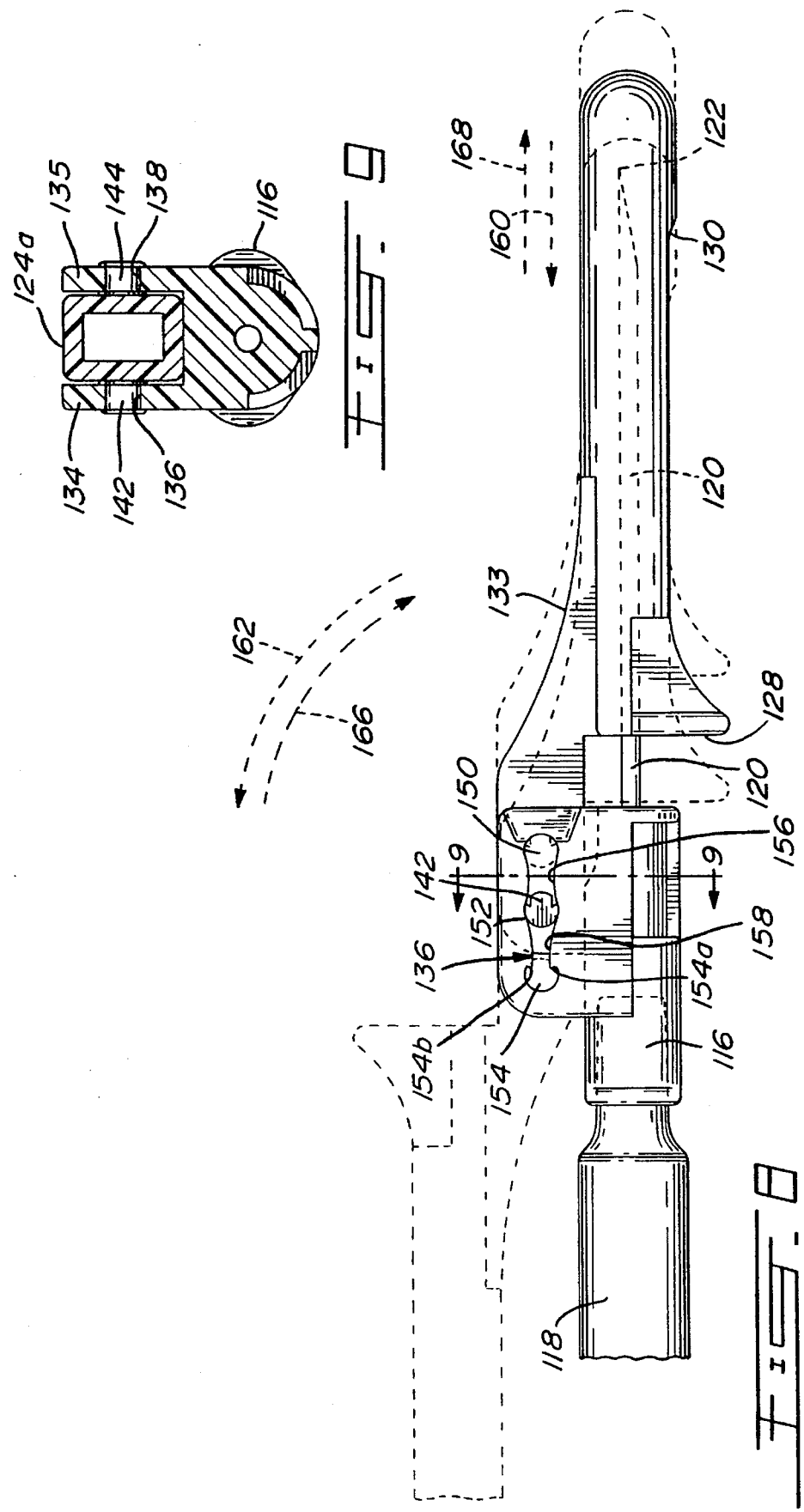

NEEDLE ASSEMBLY FOR USE WITH A SYRINGE

FIELD OF THE INVENTION

The present invention pertains to a needle assembly which is adapted to be fitted to a syringe and which comprises a needle guard, mounted to a needle holder, which can be finger manipulated using one hand only.

BACKGROUND OF THE INVENTION

Needle assemblies consisting of a needle and of a needle guard protecting the needle and being hingedly connected so that it can be finger manipulated between a needle covering position to a needle using operation are well known.

For example, U.S. Pat. No. 5,116,325 issued May 26, 1992 to Donald W. Patterson describes a needle assembly which comprises a needle device, having a needle base and a hollow needle, and a needle guard which consists of a protective sheath around the needle such that the pointed end of the needle is protected by the sheath. The assembly includes hinge components on the sheath and hinge components on the base cooperating with each other such that the needle guard is pivoted from a primary position in which the needle end is protected by the sheath to a secondary position in which the needle point is exposed for use.

However, in this assembly, the particular construction of the hinge components on the needle base and on the needle sheath is such that, when the sheath is pivoted so that the needle may be used, it can only rotate rearwardly to a position of 90° maximum to the needle covering position. This has one major drawback in that, during the needle using operation, the sheath's presence is an encumbrance to the operator.

OBJECTS AND STATEMENT OF THE INVENTION

It is an object of the present invention to provide a novel needle assembly for use with a syringe which avoids the above described problems of known needle assemblies. This is achieved by providing a needle guard which can be retracted to a complete rearward position which is substantially parallel to the longitudinal axis of the syringe and in proximity therewith.

Therefore, the present invention pertains to a needle assembly for use with a syringe which comprises:

a needle device including a needle holder and a needle having a pointed free end protruding from the holder along a longitudinal axis, the sheath defining a needle passage therein;

a needle guard including a hollow cylindrical sheath around the needle and having a first end mounted to the needle holder and an opposite closed end in proximity to the needle pointed end; and cooperating means mounted to the needle holder and the needle guard to anchor the needle guard to the holder; the cooperating means including elongate slot means extending parallel and offset to the longitudinal axis of the needle and pivot means engaged in the slot means and extending along an axis perpendicular and offset to the longitudinal axis of the needle whereby the needle guard may be pivoted about the offset axis from a first position in which the pointed end is protected by the sheath to a second position in which the needle guard extends rearwardly in substantially parallel proximity to a syringe to which is mounted the needle assembly and in which the needle point is exposed for use; the slot means defining an elongated opening whereby the pivot means may be engaged at least at two positions, including a primary position and a secondary position, and whereby the sheath is displaceable in a longitudinal direction with respect to the needle from the primary position in which the needle pointed end is protected by a portion of the sheath to the secondary position in which the needle guard may be pivoted between the first and second positions.

In one embodiment of the invention, the slot means are provided on the needle guard while the pin means are mounted on the holder.

In another embodiment, the slot means are provided on the needle holder while the pivot means are mounted on the needle guard.

In another form of the invention, the elongated opening displays three pin receiving areas corresponding to the primary and secondary positions as well as to a tertiary position in which the needle guard is fixedly secured to the needle holder after needle use.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

IN THE DRAWINGS

FIG. 1 is a top plan view of a needle assembly made in accordance with the present invention;

FIG. 2 is a side elevation thereof showing the needle assembly mounted to a syringe and with the needle guard in a locked engagement with the needle holder;

FIG. 3 is a side elevation, similar to that of FIG. 2, showing the needle guard in the needle surrounding position;

FIG. 4 is side elevation, similar to that of FIGS. 2 and 3, showing the needle guard at substantially 180° to the sheath covering position shown in FIGS. 2 and 3;

FIG. 5 is a cross sectional view as seen from line 5—5 of FIG. 3;

FIG. 6 is a cross sectional view as seen from line 6—6 of FIG. 3;

FIG. 7 is a top plan view of another embodiment of the present invention;

FIG. 8 is a side elevation of the embodiment shown in FIG. 7; and

FIG. 9 is a cross sectional view as seen from line 9—9 of FIG. 8.

DESCRIPTION OF PREFERRED EMBODIMENT

Referring to FIGS. 1 and 2, there is shown a first embodiment, generally denoted 10, of a needle assembly made in accordance with the present invention.

The needle assembly comprises a needle device 12 and a needle guard 14 pivotally mounted to one another as explained hereinbelow.

The needle device 12 comprises a needle holder 16 having an open end adapted to fit onto the open end of a syringe 18 and a needle 20 protruding from the opposite end of the holder and displaying a pointed end 22.

The needle guard 14 defines a hollow cylindrical sheath 24 surrounding the needle. The sheath has one end 24a pivotally mounted to the needle holder as detailed hereinbelow and an opposite closed end 24b in proximity to the needle pointed end 22. The underside of the sheath has a longitudinal slot 26 (see FIG. 5), the length of which extends from the opened end 28 of the sheath to an area 30 of the end 22b of the sheath. Two areas 32 and 33 on the top surface of the sheath 24 are serrated to provide frictional contact to an operator's thumb during operation as described hereinbelow.

Referring to FIG. 6, the needle holder 16 has an upper protruding portion 34 to which is anchored the rear portion 24a of the sheath. From opposite sides of this portion 34 extends a pair of pivot pins 36 and 38 which extend along an axis which is perpendicular and offset to the longitudinal axis of the needle 20, which axis is also coincident with the axis of the holder opening 40. Pivot pins 36 and 38 each protrude through a pair of elongated openings 42 and 44 provided on each side of two wing portions 46 and 48 of the sheath area 24a.

Each elongated opening 42, 44 is a longitudinal passageway defining three enlarged areas 50, 52 and 54 and two restricted passages 56 and 58 (see FIGS. 2 and 3).

As can be seen in FIG. 3 as well as in FIG. 4, the enlarged area 54 of the opening has a shape which is complementary to the shape of the pivot pins 36 and 38 so that, when the pins are in the area 54, they are locked in this position due to the engagement of the pins against the shoulders 54a and 54b of the opening.

The longitudinal axes of openings 42 and 44 are parallel, but offset, with respect to the longitudinal axis of the needle holder and syringe.

The operation of the needle assembly will now be given. When the needle assembly is mounted to a syringe for use, it is in the position shown in FIG. 3 where the pivot pins 36 and 38 are in their corresponding central enlarged areas 52 of the openings. As can be seen, in this position, the needle pointed end 22 is protected from contact as it is surrounded by the extremity 24b of the needle guard.

When it is intended to use the needle, the syringe is held in one hand with the needle holder 16 resting on the index and the thumb contacting portion 24a of the sheath. The thumb exerts a pressure on the sheath in the direction indicated by arrow 60 moving the sheath in the position shown by the dotted lines in FIG. 3. In this position, pins 36 and 38 move through passageway 56 to the enlarged circular area 50 of the opening. Applying a downward rotational force on the sheath area 24a causes the sheath to pivot rearwardly as indicated by arrow 62 in FIG. 4 until it reaches the rearward position where it is at 180° relative to its original position and where it lies in a plane parallel to the plane of the syringe holder and needle.

In FIG. 4, there are illustrated in dotted lines a syringe 18' having a larger diameter and a second syringe 18" having an even larger diameter. It will be obvious that, in these two cases, the sheath 24 will not extend in a plane entirely parallel to the axis of the syringe due to contact of the sheath with the corner area of these larger syringes.

However, in all cases, the sheath extends sufficiently rearwardly so that the sheath may be grasped together with the syringe by the hand of the user so that its presence is not an encumbrance during the needle incision operation.

The entire needle assembly, except for the needle, may be made of plastics material so that, after use, the entire needle assembly may be discarded.

After the needle incision operation, the sheath is pivoted back, again by the thumb, as indicated by arrow 66 in FIG. 2 to a needle surrounding position. To prevent further use of the needle, a locking position of the sheath to the needle holder is achieved by having the user's thumb contacting area 33 and moving the sheath rearwardly in the direction of arrow 68 until pins 36 and 38 are engaged in their corresponding areas 54 of the elongated openings. As explained above, in this position, shoulders 50a and 50b prevent any further relative displacement of the needle guard to the needle holder.

FIGS. 7–9 illustrate a second embodiment, generally denoted 110, of a needle assembly made in accordance with the present invention.

The needle assembly comprises a needle device 112 and a needle guard 114 pivotally mounted to one another as explained hereinbelow.

The needle device 112 comprises a needle holder 116 having an open end adapted to fit onto the open end of syringe 118 and a needle 120 protruding from the opposite end of the holder and displaying a pointed end 122. The needle guard 114 defines a hollow cylindrical sheath 124 surrounding the needle. The sheath has one end 124a pivotally mounted to the needle holder as detailed hereinbelow and an opposite closed end 124b in proximity to the needle point end 122. The underside of the sheath has a longitudinal slot 126, the length of which extends from the opened end 128 of the sheath to an area 130 of the end 124b of the sheath.

The needle holder 116 has a pair of upper projecting portions 134 and 135 to which is anchored the rear portion 124a of the sheath. In each of the portions 134 and 135, there is provided opposite elongated openings 136 and 138 into which is engaged a pair of opposite pins 142 and 144 integral with the sheath end 124a.

Each elongated opening 136 and 138 is a longitudinal passageway defining three enlarged area 150, 152 and 154 and two restrictive passages 156 and 158.

As can be seen in FIG. 8, the enlarged area 154 of the opening has a shape which is complementary to the shape of the pivot pin 142 so that when the pins are in the area 154, they are locked in this position due do the engagement of the pin against the shoulders 154a and 154b of the opening.

The longitudinal axes of openings 136 and 138 are parallel, but offset, with respect to the longitudinal axes of the needle holder and the syringe.

The operation of this embodiment of the needle assembly will now be given. When the needle assembly is mounted to a syringe for use, it is in the position shown in the full lines of FIG. 8 where the pivot pins 142 and 144 are in their corresponding central enlarged areas 152 of the openings. As can be seen in this position, the needle point end 122 is protected from contact as it is surrounded by the extremity 124b of the needle guard.

When it is required to use the needle, the syringe is held in one hand with the needle holder 116 resting on the index and the thumb contacting portion 124a of the sheath. The thumb exerts a pressure on the sheath in the direction indicated by arrow 160 moving the sheath in the direction shown by dotted lines in FIG. 8. In this position, pins 142 and 144 move through passageway 156 to the enlarged circular area 150 of the opening. Applying a downward rotational force on the sheath area 124a causes the sheath to pivot rearwardly as indicated by arrow 162 until it reaches the rearward position shown in dotted lines in FIG. 8 which is at 180° relative to its original position and where it lies in a plane parallel to the plane of the syringe holder and needle.

After the needle incision operation, the sheath is pivoted back, again by the thumb, as indicated by arrow 166 to a needle surrounding position. To prevent further use of the needle, a locking position of the sheath to the needle holder is achieved by the thumb contacting area 133 and moving the sheath rearwardly in the direction of arrow 168 until pins 142 and 144 are engaged in their corresponding areas 154 of the elongated openings. As explained above, in this position, shoulders 150a and 150b prevent any further relative displacement of the needle guard to the needle holder.

Although the invention has been described above with respect to two specific forms, it will be evident to a person skilled in the art that it may be modified and refined in various ways. It is therefore wished to have it understood that the present invention should not be limited in scope, except by the terms of the following claims.

The embodiments of the invention in which an exclusive property or privilege is claimed are defined as follows:

1. A needle assembly for use with a syringe comprising:

a needle device including a needle holder and a needle having a pointed free end protruding from the holder along a longitudinal axis;

a needle guard including a hollow cylindrical sheath around the needle and having a first end mounted to the needle holder and an opposite closed end in proximity to the needle pointed end said sheath defining a needle passage therein; and cooperating means mounted to said needle holder and said needle guard to anchor said needle guard to said holder; said cooperating means including elongate slot means extending parallel and offset to the longitudinal axis of said needle and pivot means engaged in said slot means and extending along an axis perpendicular and offset to the longitudinal axis of said needle whereby the needle guard may be pivoted about said offset axis from a first position in which the pointed end is protected by the sheath to a second position in which the needle guard extends rearwardly in substantially parallel proximity to a syringe to which is mounted the needle assembly, and in which the needle point is exposed for use; said slot means defining an elongated opening whereby said pivot means may be engaged at least at two positions, including a primary position and a secondary position, and whereby said sheath is displaceable in a longitudinal direction with respect to the needle from said primary position in which the needle pointed end is protected by a portion of the sheath to said secondary position in which said needle guard may be pivoted between said first and second positions.

2. A needle assembly as defined in claim 1, wherein said elongated opening includes a tertiary position, spaced longitudinally from the secondary position, in which the needle guard is in a locked engagement with said needle holder.

3. A needle assembly as defined in claim 2, wherein said slot means consist of a pair of opposite elongated openings on said needle guard and wherein said pivot means consist of a pair of pivot pins protruding from said needle holder.

4. A needle assembly as defined in claim 2, wherein said slot means consist of a pair of opposite elongated openings in said needle holder and wherein said pivot means consists of a pair of pivot pins protruding from said needle guard.

5. A needle assembly as defined in claim 3, wherein said opposite elongated openings each define a longitudinal passageway having three enlarged pin receiving areas defining said primary, secondary and tertiary positions.

6. A needle assembly as defined in claim 5, wherein said pivot pins and said enlarged area corresponding to the tertiary position have complementary cross-sectional shapes so as to define a locking engagement between the needle guard and the needle holder in said tertiary position.

7. A needle assembly as defined in claim 4, wherein said opposite elongated openings each define a longitudinal passageway having three enlarged pin receiving areas defining said primary, secondary and tertiary positions.

8. A needle assembly as defined in claim 7, wherein said pivot pins and said enlarged area corresponding to the tertiary position have complementary cross-sectional shapes so as to define a locking engagement between the needle guard and the needle holder in said tertiary position.

9. A needle assembly as defined in claim 1, wherein a portion of the needle guard in the area of said cooperating means has a frictional surface to facilitate finger manipulation of said needle guard.

* * * * *